United States Patent [19]

Roth

[11] Patent Number: 6,156,547
[45] Date of Patent: *Dec. 5, 2000

[54] APPARATUS FOR THE SYNTHESIS OF SACCHARIDE COMPOSITIONS

[75] Inventor: Stephen Roth, Gladwyne, Pa.

[73] Assignee: NEOSE Pharmaceuticals, Inc., Horsham, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/745,840

[22] Filed: Nov. 8, 1996

Related U.S. Application Data

[63] Continuation of application No. 08/215,727, Mar. 22, 1994, Pat. No. 5,583,042, which is a continuation-in-part of application No. 08/163,534, Dec. 9, 1993, abandoned, which is a continuation of application No. 07/955,687, Oct. 2, 1992, Pat. No. 5,288,637, which is a continuation of application No. 07/683,810, Apr. 11, 1991, Pat. No. 5,180,674, which is a continuation-in-part of application No. 07/509,560, Apr. 16, 1990, abandoned.

[51] Int. Cl.$^7$ .............................. C12P 19/18; C12P 19/04
[52] U.S. Cl. ............................... 435/97; 435/101; 435/84; 536/21
[58] Field of Search ................................ 435/97, 101, 84; 536/21

[56] References Cited

PUBLICATIONS

Lidholt et al, Biochem. J. 261:999–1007 (1989).

*Primary Examiner*—Francisco Prats
*Attorney, Agent, or Firm*—Oblon, Spivak, McClelland, Maier & Neustadt, P.C.

[57] ABSTRACT

This invention relates to an apparatus containing specific binary combinations of glycosyltransferases, for the synthesis of specific saccharide compositions such as, for example, oligosaccharides, polysaccharides, glycolipids, and glycopeptides.

3 Claims, No Drawings

APPARATUS FOR THE SYNTHESIS OF SACCHARIDE COMPOSITIONS

This is a Continuation, of application Ser. No. 08/215,727 filed on Mar. 22, 1994; now U.S. Pat. No. 5,583,042 which is a Continuation-in-Part of application Ser. No. 08/163,534, filed on Dec. 9, 1993, Abandoned; which is a Continuation of application Ser. No. 07/955,687, filed on Oct. 2, 1992, now U.S. Pat. No. 5,288,637, which is a Continuation of Ser. No. 07/683,810, filed on Apr. 11, 1991, now U.S. Pat. No. 5,180,674, which is a Continuation-in-Part of application Ser. No. 07/509,560, filed on Apr. 16, 1990, Abandoned.

BACKGROUND OF THE INVENTION

1. Field of the Invention

This invention relates to an apparatus containing specific binary combinations of glycosyltransferases, for the synthesis of specific saccharide compositions such as, for example, oligosaccharides, polysaccharides and glycopeptides.

2. Discussion of the Background

The term "carbohydrate" embraces a wide variety of chemical compounds having the general formula $(CH_2O)_n$, such as polysaccharides. Oligosaccharides are chains composed of saccharide units, which are alternatively known as sugars. These saccharide units can be arranged in any order and the linkage between two saccharide units can occur in any of approximately ten different ways. As a result, the number of different possible stereoisomeric oligosaccharide chains is enormous.

Of all the biological polymer families, oligosaccharides and polysaccharides have been the least well studied, due in considerable part to the difficulty of sequencing and synthesizing their often complex sugar chains. Although the syntheses of oligonucleotides and polypeptides are well developed, corresponding synthetic techniques for synthesizing oligosaccharides have been slow to develop.

Numerous classical techniques for the synthesis of carbohydrates have been developed, but these techniques suffer the difficulty of requiting selective protection and deprotection. Organic synthesis of oligosaccharides is further hampered by the lability of many glycosidic bonds, difficulties in achieving regioselective sugar coupling, and generally low synthetic yields. These difficulties, together with the difficulties of isolating and purifying carbohydrates and of analyzing their structures, has made this area of chemistry a most demanding one.

Much research effort has been devoted to carbohydrates and molecules comprising carbohydrate fragments, such as glycolipids and glycopeptides. Research interest in such moieties has been large due to the recognition that interactions between proteins and carbohydrates are involved in a wide array of biological recognition events, including fertilization, molecular targeting, intercellular recognition, and viral, bacterial, and fungal pathogenesis. It is now widely appreciated that the oligosaccharide portions of glycopeptides and glycolipids mediate recognition between cells and cells, between cells and ligands, between cells and the extracellular matrix, and between cells and pathogens.

These recognition phenomena can likely be inhibited by oligosaccharides having the same sugar sequence and stereochemistry found on the active portion of a glycoprotein or glycolipid involved in cell recognition. The oligosaccharides are believed to compete with the glycopeptides and glycolipids for binding sites on receptor proteins. For example, the disaccharide galactosyl β 1–4 N-acetylglucosamine is believed to be one component of the glycopeptides which interact with receptors in the plasma membrane of liver cell. Thus, to the extent that they compete with potentially harmful moieties for cellular binding sites, oligosaccharides and other saccharide compositions have the potential to open new horizons in pharmacology, diagnosis, and therapeutics.

In mammalian systems, eight monosaccharides activated in the form of nucleoside mono- and diphosphate sugars provide the building blocks for most oligosaccharides: UDP-Glc, UDP-GlcUA, UDP-GlcNAc, UDP-Gal, UDP-GalNAc, GDP-Man, GDP-Fuc and CMP-NeuAc. These are the intermediates of the Leloir pathway. A much larger number of sugars (e.g., xylose, arabinose) and oligosaccharides are present in microorganisms and plants.

Two groups of enzymes are associated with the in vivo synthesis of oligosaccharides. The enzymes of the Leloir pathway are the largest group. These enzymes transfer sugars activated as sugar nucleoside phosphates to a growing oligosaccharide chain. Non-Leloir pathway enzymes transfer carbohydrate units activated as sugar phosphates, but not as sugar nucleoside phosphates.

Two strategies have been proposed for the enzyme-catalyzed in vitro synthesis of oligosaccharides. See Toone et al, *Tetrahedron Reports* (1990) (45)17:5365–5422. The first strategy proposes to use glycosyltransferases. The second proposes to use glycosidases or glycosyl hydrolases.

Glycosyltransferases catalyze the addition of activated sugars, in a stepwise fashion, to a protein or lipid or to the non-reducing end of a growing oligosaccharide. A very large number of glycosyltransferases appear to be necessary to synthesize carbohydrates. Each NDP-sugar residue requires a distinct class of glycosyltransferase and each of the more than one hundred glycosyltransferases identified to date appears to catalyze the formation of a unique glycosidic linkage. To date, the exact details of the specificity of the glycosyltransferases are not known. It is not clear, for example, what sequence of carbohydrates is recognized by most of these enzymes.

Much hope has been put on future developments in genetic engineering (i.e., cloning) of enzymes, particularly since several glycosyltransferases have already been cloned, including galacto-, fucosyl-, and sialyltransferases. It is hoped that future advances in cloning techniques will speed the cloning of other glycosyltransferases and enhance their stability.

Accordingly, in light of their potential uses and the difficulty or impossibility to obtain them in sufficient quantities, there exists a long-felt need for specific synthetic methods for the production of specific oligosaccharides, polysaccharides and glycopeptides and similar species in an efficient, cost effective, stereospecific, and generally applicable manner.

SUMMARY OF THE INVENTION

It is an object of the present invention to provide an apparatus containing a specific binary combination of glycosyltransferases, for the synthesis of a specific saccharide composition such as, for example, oligosaccharides, polysaccharides and glycopeptides.

These and other objects are achieved by the present invention, which provides for an apparatus containing a specific binary combination of glycosyltransferases for preparing specific oligosaccharides, polysaccharides, glycopeptides, and other saccharide compositions. Through the isolation of specific glycosyltransferases, specific saccharide compositions can be synthesized through the action on specific acceptor molecules.

DETAILED DESCRIPTION OF THE PREFERRED EMBODIMENTS

As employed herein, the term "saccharide composition" is intended to include any chemical moiety having a saccharide unit within its structure. Sugars, carbohydrates, saccharides, molosaccharides, oligosaccharides, polysaccharides and glycopeptides provide examples of saccharide compositions. Mixtures and solutions comprising such moieties are also saccharide compositions.

Saccharide compositions are prepared by using the apparatus according to this invention by the enzyme-facilitated transfer of saccharide units from donor moieties to acceptor moieties. It will be appreciated that such transfer occurs upon contacting the acceptor and donor moieties with a glycosyltransferase, and typically results in covalently bonding of the acceptor moiety and the saccharide unit stereoselectively, that is, in but one stereoisomeric form.

The specific saccharide compositions prepared by using the apparatus in accordance with this invention are useful as diagnostics, therapeutics, pharmaceuticals and intermediates in the preparation of higher oligosaccharides which are useful as diagnostics and therapeutics.

According to one embodiment of the present invention, an apparatus containing a β-1,3 N-acetylglucosaminyltransferase, capable of transferring glcNAc to either lactose or lactosamine and a β-1,3 galactosyltransferase capable of transferring gal to glcNAc β 1,3 gal β-1,4 glc or glcNAc β-1,3 gal β-1,4 glcNAc is provided. The appropriate β-1,3 N-acetylglucosaminyltransferase is isolated from mammalian sera purified by DEAE chromatography and by affinity chromatography on wheat germ agglutinin and UDP columns. The appropriate β-1,3 galactosyltransferase is isolated from the detergent-treated trachea tissue from dogs and other mammals. Purification is achieved by affinity columns of UDP and immobilized glcNAc β-1,3 gal β-1,4 glc or glcNAc β-1,3 gal β-1,4 glcNAc. The isolated and purified enzymes are preferably immobilized separately on either Affigel or Ultrogel matrices and placed in an apparatus with the appropriate sugar donor. Operation of this apparatus is as appropriate, typically at a temperature of 37° C., in the presence of manganese ions at a concentration of from 1–15 mmol/l. The product produced by this apparatus is a Type I polylactosamine.

According to another embodiment of the present invention, an apparatus containing an α-2,3 sialyltransferase, capable of transferring sialic acid to polylactosamine and an α-1,4 fucosyltransferase capable of transferring fuc to polylactosamine which has been substituted with an α-2,3-sialic acid is provided. The appropriate α-2,3 sialyltransferase is isolated from detergent treated liver SW1116 cells, purified by DEAE chromatography and by affinity chromatography on immobilized polylactosamine and CMP columns. The appropriate α-1,4 fucosyltransferase is isolated from detergent-treated human colon cancer cells [COLO 205]. Purification is achieved by affinity columns of GDP and immobilized Type I polylactosamine. The isolated and purified enzymes are preferably immobilized separately on either Affigel or Ultrogel matrices and placed in an apparatus with CMP-NeuAc and/or GDP-Fuc. Operation of this apparatus is as appropriate, typically at a temperature of 37° C., in the presence of manganese ions at a concentration of from 1–15 mmol/l. The product produced by this apparatus is sialyl Lewis$^a$.

According to another embodiment of the present invention, an apparatus containing an α-1,4 galactosyltransferase, capable of transferring gal to either lactose or a lactoside (i.e., gal β-1,4 glc-1-R) and a β-1,3 N-acetylgalactosaminyltransferase capable of transferring galNAc to gal α-1,4 gal β-1,4 glc-1-R or gal α-1,4 gal β-1,4 glc-1-R is provided. The appropriate α-1,4 galactosyltransferase is isolated from human placenta or human plasma, purified by DEAE chromatography and by affinity chromatography on immobilized lactose and UDP columns. The appropriate β-1,3 N-acetylgalactosaminyltransferase is isolated from detergent-treated human kidney tissue. Purification is achieved by affinity columns of UDP and immobilized gal α-1,4 gal β-1,4 glc-1-R. The isolated and purified enzymes are preferably immobilized separately on either Affigel or Ultrogel matrices and placed in an apparatus with UDP-gal and/or UDP-galNAc. Operation of this apparatus is as appropriate, typically at a temperature of 37° C., in the presence of manganese ions at a concentration of from 1–15 mmol/l. The product produced by this apparatus is an intermediate in the preparation of the globo-series oligosaccharides.

According to another embodiment of the present invention, an apparatus containing a β-1,4 N-acetylgalactosaminyltransferase, capable of transferring galNAc to either lactose or a lactoside and a β-1,3 galactosyltransferase capable of transferring gal to galNAc β-1,4 gal β-1,4 glc-1-R is provided. The appropriate β-1,4 N-acetylgalactosaminyltransferase is isolated from detergent-treated calf brain tissue, purified by DEAE chromatography and by affinity chromatography on immobilized lactose and UDP columns. The appropriate β-1,3 galactosyltransferase is isolated from embryonic chick brains. Purification is achieved by affinity columns of UDP and immobilized galNAc β-1,4 gal β-1,4 glc-1-R. The isolated and purified enzymes are preferably immobilized separately on either Affigel or Ultrogel matrices and placed in an apparatus with UDP-galNAc and/or UDP-gal. Operation of this apparatus is as appropriate, typically at a temperature of 37° C., in the presence of manganese ions at a concentration of from 1–15 mmol/l. The product produced by this apparatus is an intermediate in the preparation of the ganglio-series oligosaccharides.

According to another embodiment of the present invention, an apparatus containing a β-1,4 galactosyltransferase, capable of transferring gal to either lactose or a lactoside and a β-1,3 galactosyltransferase capable of transferring gal to gal β-1,4 gal β-1,4 glc-1-R is provided. The appropriate β-1,4 galactosyltransferase is isolated from hog gastric mucosa treated with Triton X-100, 1%, purified by DEAE chromatography and by affinity chromatography on immobilized lactose and UDP columns. The appropriate β-1,3 galactosyltransferase is isolated from hog gastric mucosa. Purification is achieved by affinity columns of UDP and immobilized gal β-1,4 gal β-1,4 glc-1-R. The isolated and purified enzymes are preferably immobilized separately on either Affigel or Ultrogel matrices and placed in an apparatus with UDP-gal. Operation of this apparatus is as appropriate, typically at a temperature of 37° C., in the presence of manganese ions at a concentration of from 1–15 mmol/l. The product produced by this apparatus is an intermediate in the preparation of the muco-series oligosaccharides.

According to another embodiment of the present invention, an apparatus containing an α-1,3 galactosyltransferase, capable of transferring gal to either lactose or a lactoside and a β-1,3 N-acetylgalactosaminyltransferase capable of transferring galNAc to gal α-1,3 gal β-1,4 glc-1-R is provided. The appropriate α-1,3 galactosyltransferase is isolated from detergent-treated rat intestine tissue, purified by DEAE chromatography and by affinity chromatography on immobilized lactose and UDP columns. The appropriate β-1,3 N-acetylgalactosaminyltransferase is isolated from detergent-treated lymphosarcoma tissue. Purification is achieved by affinity columns of UDP and immobilized gal α-1,3 gal β-1,4 glc-1-R. The isolated and purified enzymes are preferably immobilized separately on either Affigel or Ultrogel matrices and placed in an apparatus with UDP-gal and/or UDP-galNAc. Operation of this apparatus is as appropriate, typically at a temperature of 37° C., in the presence of manganese ions at a concentration of from 1–15 mmol/l. The product produced by this apparatus is an intermediate in the preparation of the globoiso-series oligosaccharides.

According to another embodiment of the present invention, an apparatus containing an α-1 N-acetylgalactosaminyltransferase, capable of transferring galNAc to either serine or threonine and a -1,3 galactosyltransferase capable of transferring gal to galNAc β-1 serine or galNAc β-1 threonine is provided. The appropriate α-1 N-acetylgalactosaminyltransferase is isolated from detergent-treater bovine intestine or placenta tissue, purified by DEAE and CM chromatography and by affinity chromatography on UDP columns. The appropriate β-1,3 galactosyltransferase is isolated from detergent-treated submaxillary glands. Purification is achieved by affinity columns of UDP and immobilized galNAc β-1 serine or galNAc β-1-threonine. The isolated and purified enzymes are preferably immobilized separately on either Affigel or Ultrogel matrices and placed in an apparatus with UDP-galNAc and/or UDP-gal. Operation of this apparatus is as appropriate, typically at a temperature of 37° C., in the presence of manganese ions at a concentration of from 1–15 mmol/l. The product produced by this apparatus is an intermediate in the preparation of the mucin-type oligosaccharides.

According to another embodiment of the present invention, an apparatus containing a β-1,6 N-acetylglucosaminyltransferase, capable of transferring glcNAc to the galNAc of gal β-1,3 galNAc α-1-O-linked serine or gal β-1,3 galNAc α-1-O-linked threonine (i.e. mucin-type galNAc) and a β-1,4 galactosyltransferase capable of transferring gal to the glcNAc of gal β-1,3 galNAc(glcNAc β-1,6)α-1-O-linked serine is provided. The appropriate β-1,6 N-acetylglucosaminyltransferase is isolated from pig gastric mucosa, serum or ovary tissue, purified by DEAE chromatography and by affinity chromatography on immobilized mucin-type galNAc and UDP columns. The appropriate β-1,4 galactosyltransferase is isolated from procine submaxillary glands. Purification is achieved by affinity columns of immobilized UDP or immobilized gal β-1,3 galNAc(glcNAc β-1,6) α-1-O-linked threonine. The isolated and purified enzymes are preferably immobilized separately on either Affigel or Ultrogel matrices and placed in an apparatus with UDP-glcNAc and/or UDP-gal. Operation of this apparatus is as appropriate, typically at a temperature of 37° C., in the presence of manganese ions at a concentration of from 1–15 mmol/l. The product produced by this apparatus is a branched oligosaccharide which is an intermediate in the production of the mucin-lacNAc series oligosaccharides.

According to another embodiment of the present invention, an apparatus containing an α-1,4 N-acetylglucosaminyltransferase, capable of transferring glcNAc to heparins and heparan sulfates and a β-1,4 glucuronyltransferase capable of transferring glucuronic acid to glcNAc β-1,4 substituted heparin or heparan sulfate is provided. The appropriate α-1,4 N-acetylglucosaminyltransferase is isolated from detergent-treated mastocytomas tissue or plasma, purified by DEAE chromatography and by affinity chromatography on immobilized heparin or heparan sulfate and UDP columns. The appropriate β-1,4 glucuronyltransferase is also isolated from mastocytomas tissue or plasma. Purification is achieved by affinity columns of UDP and immobilized glcNAc β-1,4 substituted heparin or heparan sulfate. The isolated and purified enzymes are preferably immobilized separately on either Affigel or Ultrogel. matrices and placed in an apparatus with UDP-glcNAc and/or UDP-glucuronic acid. Operation of this apparatus is as appropriate, typically at a temperature of 37° C., in the presence of manganese ions at a concentration of from 1–15 mmol/l. The product produced by this apparatus is an elongated heparin or elongated heparan sulfate.

According to another embodiment of the present invention, an apparatus containing a β-1,4 N-acetylgalactosaminyltransferase, capable of transferring galNAc to chondroitins and chondroitin sulfates and a β-1,3 glucuronyltransferase capable of transferring glucuronic acid to galNAc β-1,4 substituted chondroitins and chondroitin sulfates is provided. The appropriate β-1,4 N-acetylgalactosaminyltransferase is isolated prom detergent-treated cartilage tissue or chondrosarcomas tissue, purified by DEAE chromatography and by affinity chromatography on immobilized chondroitin or immobilized chondroitin sulfate and UDP columns. The appropriate β-1,3 glucuronyltransferase is isolated from detergent-treated cartilage tissue or chondrosardomas tissue. Purification is achieved by affinity columns of UDP and immobilized galNAc β-1,4 substituted chondroitins or chondroitin sulfates. The isolated and purified enzymes are preferably immobilized separately on either Affigel or Ultrogel matrices and placed in an apparatus with UDP-galNAc and/or UDP-glucuronic acid. Operation of this apparatus is as appropriate, typically at a temperature of 37° C., in the presence of manganese ions at a concentration of from 1–15 mmol/l. The product produced by this apparatus is an elongated chondroitin or chondroitin sulfate.

According to another embodiment of the present invention, an apparatus containing a β-1,4 N-acetylglucosaminyltransferase, capable of transferring glcNAc to hyaluronic acids and a β-1,3 glucuronyltransferase capable of transferring glucuronic acid to glcNAc β-1,4 substituted hyaluronic acid is provided. The appropriate β-1,4 N-acetylglucosaminyltransferase is isolated from detergent-treated cartilage tissue or connective tissue, purified by DEAE chromatography and by affinity chromatography on immobilized hyaluronic acid and UDP columns. The appropriate β-1,3 glucuronyltransferase is isolated from detergent-treated cartilage tissue or connective tissue. Purification is achieved by affinity columns of UDP and immobilized glcNAc β-1,4 substituted hyaluronic acid. The isolated and purified enzymes are preferably immobilized separately on either Affigel or Ultrogel matrices and placed in an apparatus with UDP-glcNAc and/or UDP-glucuronic acid. Operation of this apparatus is as appropriate, typically at a temperature of 37° C., in the presence of manganese ions at a concentration of from 1–15 mmol/l. The product produced by this apparatus is an elongated hyaluronic acid.

According to another embodiment of the present invention, an apparatus containing an α-1,2 fucosyltransferase, capable of transferring fuc to the terminal gal of Type II polylactosamine and an α-1,3 fucosyltransferase capable of transferring fuc to the penultimate glcNAc of Type II polylactosamine is provided. The appropriate α-1,2 fucosyltransferase, capable of transferring fuc to the terminal gal of polylactosamine is isolated from plasmas and many human tumor cell lines such as COLO 201, purified by DEAE chromatography and by affinity chromatography on immobilized polylactosamine and GDP columns. The appropriate α-1,3 fucosyltransferase capable of transferring fuc to the penultimate glcNAc of previously fucosylated polylactosamine is also isolated from plasmas and many human tumor cell lines, such as COLO 205, a human colon tumor cell line. Purification is achieved by affinity columns of GDP and immobilized polylactosamine. The isolated and purified enzymes are preferably immobilized separately on either Affigel or Ultrogel matrices and placed in an apparatus with two or more equivalents of GDP-fuc. Operation of this apparatus is as appropriate, typically at a temperature of 37° C., in the presence of manganese ions at a concentration of from 1–15 mmol/l The product produced by this apparatus is Lewis$^y$.

According to another embodiment of the present invention, an apparatus containing a β-1,4 galactosyltransferase, capable of transferring gal to galNAc or glcNAc and an α-1,3 galactosyltransferase capable of transferring gal to gal β-1,4 galNAc or gal β-1,4 glcNAc is provided. The appropriate β-1,4 galactosyltransferase is isolated from human or bovine milk, purified by DEAE chromatography and by affinity chromatography on immobilized galNAc or immobilized glcNAc and UDP columns. The appropriate α-1,3 galactosyltransferase capable of transferring gal to gal β-1,4 galNAc or gal β-1,4 glcNAc is isolated from detergent-treated murine F9 cells. Purification is achieved by affinity columns of UDP and immobilized gal β-1,4 gal β-1,4 galNAc or gal β-1,4 gal β-1,4 glcNAc. The isolated and purified enzymes are preferably immobilized separately on either Affigel or Ultrogel matrices and placed in an apparatus with two or more equivalents of UDP-gal. Operation of this apparatus is as appropriate, typically at a temperature of 37° C., in the presence of manganese ions at a concentration of from 1–15 mmol/l. The product produced by this apparatus is the gal α gal epitope.

Also provided by the invention are reaction conditions and co-reagents as may be necessary and sufficient to effect the covalent bonding of the specific saccharide unit to the specific acceptor moiety. In general, it is preferred to employ saccharide nucleotides as donor moieties. Uridine, guanosine, and cytidine phosphate materials terminated by the saccharide units to be donated preferably comprise the donor moieties.

As identified above, the specific enzymes used in the present apparatus are isolated from specifically identified sources. The enzymes are purified from homogenates by affinity chromatography using the acceptor moiety as the affinity ligand. That is, the homogenate is passed over a solid matrix having immobilized thereon the acceptor moiety under conditions which cause the glycosyltransferase to bind to the acceptor moiety. The solid support matrix having the glycosyltransferase bound thereto is then washed. This is followed by an elution step in which the glycosyltransferase is desorbed from the solid support matrix and collected. As known, the absorbed glycosyltransferase may be eluted, for example, by passing an aqueous salt (e.g. NaCl) solution over the solid support matrix. The same procedure can be followed using the appropriate immobilized nucleotide, in what is termed a donor UDP column.

In actual practice of the apparatus of the invention, the "enzyme" purified from the homogenate by affinity chromatography and which is used to attach a preselected saccharide unit onto the acceptor moiety comprises a mixture of various glycosyltransferases which have been purified away from other extraneous biological material present in the homogenate which includes enzymes which can interfere with the desired activity of the purified glycosyltransferases. Thus, the "glycosyltransferase" used in accordance with the present invention is frequently a mixture of various glycosyltransferases. If desired, this material may be further purified, with a single purified glycosyltransferase being isolated and used in the process of the present invention, but such further purification is generally not necessary.

In accordance with the present invention, a specific acceptor moiety is provided which is capable of being covalently bound to a preselected saccharide unit.

The saccharide unit to be transferred to an acceptor moiety is provided by a donor moiety for the saccharide unit. A donor moiety according to this invention includes the saccharide unit to be transferred and is capable of providing that saccharide unit to the acceptor moiety when contacted by the acceptor moiety and the appropriate glycosyltransferase. Preferred donor moieties are saccharide nucleotides, such as saccharide-terminated uridine phosphates, saccharide-terminated guanosine phosphates, and saccharide-terminated cytidine phosphates.

It will be appreciated that donor moieties are preferred to be capable of readily providing their component saccharide unit to an acceptor moiety when placed in contact therewith and with a glycosyltransferase. For example, uridine diphosphate galactose is preferred for transferring galactose to N-acetylglucosamine, while cytidine monophosphate N-acetylneuraminic acid is preferred for transferring N-acetylneuraminic acid, a sialic acid, to galactosyl β 1–4 N-acetylglucosamine.

In a preferred method of isolation, the specific acceptor moiety is immobilized as, for example, on a solid support. It will be appreciated that the term "solid support" includes semi-solid supports as well. Once immobilized, the acceptor moiety is contacted with a mixture containing the specific glycosyltransferases, such as one comprising naturally-occurring cell homogenate. Since an immobilized acceptor moiety will bind the enzyme specific for it, this system is then monitored for acceptor-bound enzyme.

Monitoring for acceptor-bound enzyme may be carried out as follows. The cell homogenate is passed over the immobilized acceptor moiety. This may be achieved, for example, by passing the cell homogenate over a column charged with immobilized acceptor moiety. The column is then washed and the amount of protein which passes through the column charged with immobilized acceptor moiety is monitored. When no more protein is detected, an aqueous salt solution eluant is passed through the column to elute the enzyme. The eluant obtained is then assayed for the presence of glycosyltransferase(s). The assays which can be used are noted above, i.e., the methods described by Furukawa et al, Roth et al and Benau et al.

After the glycosyltransferase is isolated, it is contacted with the acceptor moiety and donor moiety under conditions sufficient to effect transfer and covalent bonding of the saccharide unit to the acceptor moiety. It will be appreciated that the conditions of, for example, time, temperature, and pH appropriate and optimal for a particular saccharide unit transfer can be determined by one of skill in the art through routine experimentation. Certain co-reagents may also prove useful in effecting such transfer. For example, it is preferred that the acceptor and donor moieties be contacted with the glycosyltransferase in the presence of divalent cations, especially manganese cations such as may be provided by $MnCl_2$.

In a preferred embodiment, the specific glycosyltransferase is immobilized by attachment to a solid support and the acceptor and donor moieties to be contacted therewith are added thereto. As discussed above, the glycosyltransferase used in accordance with the present invention is frequently a mixture of glycosyltransferases containing at least one glycosyltransferase possessing the desired activity, but purified single glycosyltransferases may also be used in accordance with the present invention. In this preferred embodiment, either the mixture of glycosyltransferases or the purified single glycosyltransferase may be immobilized. Alternatively, the glycosyltransferase, donor and acceptor are each provided in solution and contacted as solutes.

A preferred procedure for immobilization of glycosyltransferases and of acceptor moieties, where necessary, is based on the copolymerization in a neutral buffer of a water soluble prepolymer such as poly(acrylamide-co-N-acryloxysuccinimide (PAN), a cross-linking diamine such as triethylenetetramine, and the glycosyltransferase, as disclosed by Pollack et al., *J. Am. Chem. Soc.* (1980) 102:6324–36. The immobilization of the enzymes on PAN is useful because small amounts of enzyme can be used, high yields of enzyme activity are obtained, and the bond between enzyme and polymer is stable.

More preferred methods of immobilization include immobilization of the glycosyltransferase amino groups onto solid support oxirane groups (see, e.g., Chun et al, *Enzyme Enq.* (1980) 5:457–462) or onto cyanogen bromide activated "SEPHADEX" or "SEPHAROSE" (Axen et al, Nature (1967) 214:13021304). Gycosyltransferases can also be immobilized onto "AFFIGEL", an N-Hydroxy succinimide activated support.

In a preferred embodiment, the glycosyltransferase is immobilized from a moderately purified composition containing the glycosyltransferase. Extremely pure enzyme preparations (i.e., with specific activities in the range of 1 nmole transferred per $\mu$g protein per minute of incubation) are less efficiently immobilized covalently to solid supports, in that the percent derivatization is lower, compared to 10 or 100 times less pure preparations.

It will be appreciated that impairment of the active sites of the glycosyltransferase due to immobilization should be avoided. The inventor observed that contaminating enzyme activities tend to disappear during the immobilization process as compared to the activity of the glycosyltransferase of interest which is specifically protected during the immobilization process. During the immobilization process the glycosyltransferase may be protected by the cation required by the enzyme, the nucleotide recognized by the enzyme, and the acceptor recognized by the enzyme. For example, a galactosyl transferase may be protected with $Mn^{2+}$, N-acetylglucosamine and UDP during the immobilization, regardless of which immobilization method is used. In this way, contaminating proteases are not protected in any way during the immobilization process.

Because only the desired glycosyltransferase is protected during the immobilization process, enzymes that interfere with the synthesis of the target saccharide composition tend to be lost. Examples of interfering enzymes are proteases, which would otherwise attack the desired glycosyltransferase, glycosidases, which would otherwise attack the product saccharide and pyrophosphatases which would otherwise attack sugar nucleotides.

The present invention provides an apparatus suitable for use in accordance with the present invention for the glycosyltransferase catalyzed synthesis of a saccharide composition.

In a very basic embodiment the apparatus of the present invention contains one reaction chamber in which both of the glycosyltransferases, the preselected saccharide units and the initial acceptor moiety are combined. Due to the specificity of the glycosyltransferases, this mixture, given sufficient time, will produce the saccharide composition of the present invention.

The reactor is equipped with inlet means suitable for introducing the acceptor moiety and the preselected saccharide units into the reactor such that the saccharide composition is synthesized. Preferably, the inlet means is suitable for also introducing into the reactor the glycosyltransferases which are themselves preferably immobilized. The outlet means permits discharging the saccharide composition from the reactor.

An embodiment of this apparatus is a column-type reactor charged with a solid support matrix. The various glycosyltransferases (enzymes 1, 2,) used in the process may be either randomly distributed throughout the solid support matrix or they may be arranged in zones. The initial acceptor moiety and the preselected saccharide unit are charged into the reactor via the inlet means and passed through the solid support matrix whereupon the saccharide composition is produced due to the action of the specific glycosyltransferases and recovered via the outlet means.

When the glycosyltransferases are arranged in a plurality of reaction zones, a means for purifying the intermediate product formed in the preceding reaction zone may be included. The means for purifying is placed in fluid communication between the reaction zones. Suitable means include ion exchange columns and chromatography columns.

In the apparatus of the present invention, none, one or both of the glycosyltransferases may be immobilized onto a solid support. The immobilized enzymes may be placed in the same reaction zone or separate reaction zones, depending on the optimum reaction conditions required for the specific enzyme.

In another embodiment the initial acceptor moiety and the preselected saccharide unit to be attached to the initial acceptor moiety are charged at the top of the solid support matrix, with the glycosyltransferases specific to the addition of each preselected saccharide units being arranged in corresponding zones along the direction of flow of the reaction mixture. The various preselected saccharide units are then individually added at correspondingly appropriate locations along the flow of the reaction mixture.

In another preferred embodiment, the reactor comprises two reaction zones serially connected so as to be in sequential fluid communication with each other. Each reaction zone contains one glycosyltransferase specific to catalyze the bonding of a particular preselected saccharide unit onto the intermediate product formed in the preceding reaction zone.

In accordance with this embodiment the initial acceptor moiety (A) and the first preselected saccharide unit (B) to be attached to the acceptor moiety are passed through the first reaction zone which comprises a glycosyltransferase specific to catalyze the bonding of the first preselected saccharide unit onto the initial acceptor moiety thus producing a first intermediate product. This first intermediate product is then transferred to the second reaction zone where it is combined with the second preselected saccharide unit (X) and the second glycosyltransferase specific to catalyze the bonding of the second preselected saccharide unit with the first intermediate product formed.

In another preferred embodiment, means for purifying each intermediate product formed from the reaction mixture emanating from any given reaction zone are situated in fluid communication and between each of the reaction zones. The means for purifying, which may comprise, e.g., an ion exchange resin, remove contaminants in the reaction mixtures which inhibit the efficiency of the bonding of the next preselected saccharide unit onto the intermediate product formed.

Additional objects, advantages, and novel features of this invention will become apparent to those skilled in the art upon examination of the following examples thereof, which are not intended to be limiting.

EXAMPLE 1

Enzyme Immobilization
N-acetylglucosaminyltransferase:

300 mgs of AFFIGEL-10 or 15 (1.2 ml) are washed three times with deionized water, and then three times with aseptic Hepes-buffered water. One ml of the enzyme preparation is combined aseptically with the beads along with UDP, lactose, $MnCl_2$, (final concentrations: 10, 25, and 10 mM, respectively) and a drop of chloroform in a Hepes-buffered solution. The beads are gently agitated at 4° C. for 4 hours. Aliquots are taken and assayed periodically. To stop the derivatization, the beads are washed three times with an aseptic buffer, and stored in buffer, in the cold, with UDP, lactose, $MnCl_2$, and chloroform.
Galactosyltransferase 3.75 grams of beads are washed three times with deionized water, and then three times with aseptic Hepes-buffered water. The beads are added to 3-mls of the enzyme preparation (in both cases, optimum derivatization occurs at about 1 mg protein per 200 mgs beads) along with UDP, GlcNAc, $MnCl_2$, (final concentrations are all 10 mill) and a drop of chloroform in a Hepes-buffered solution. Derivatization and storage are as described above, except that the GlcNAc is used with the galactosyltransferase in place of lactose, which is the acceptor for the N-acetylglucosaminyltransferase.

EXAMPLE 2

Synthesis of Type I Polylactose

A β-1,3 N-acetylglucosaminyltransferase is isolated from mammalian sera purified by DEAE chromatography and by affinity chromatography on wheat germ agglutinin and UDP columns. A β-1,3 galactosyltransferase is isolated from detergent-treated trachea tissue from dogs. Purification is achieved by affinity columns of UDP and immobilized glcNAc β-1,3 gal β-1,4 glc-1-R. The isolated and purified enzymes are immobilized on an Affigel matrix and placed in an apparatus with UDP-glcNAc and UDP-gal along with lactose. This apparatus is operated at a temperature of 37° C., in the presence of manganese ions at a concentration of from 1–15 mmol/l for 36 h. The resulting product is isolated by ion-exchange chromatography.

EXAMPLE 3

Synthesis of Sialyl Lewis$^a$

An α-2,3 sialyltransferase is isolated from detergent treated liver SW1116 cells and purified by DEAE chromatography and affinity chromatography on immobilized polylactosamine and CMP columns. An α-1,4 fucosyltransferase is isolated from detergent-treated human colon cancer cells [COLO 205]. Purification is achieved by affinity columns of GDP and immobilized Type I polylactosamine. The isolated and purified enzymes are immobilized separately on a Ultrogel matrix and placed in an apparatus with CMP-NeuAc, GDP-Fuc and polylactose. This apparatus is operated at a temperature of 37° C., in the presence of manganese ions at a concentration of from 1–15 mmol/l for 48 h. The resulting product is isolated by ion-exchange chromatography.

EXAMPLE 4

Synthesis of a Globo-series Oligosaccharide

An α-1,4 galactosyltransferase is isolated from human plasma, purified by DEAE chromatography and by affinity chromatography on immobilized lactose and UDP columns. A β-1,3 N-acetylgalactosaminyltransferase is isolated from detergent-treated human kidney tissue. Purification is achieved by affinity columns of UDP and immobilized gal α-1,4 gal β-1,4 glc-1-R. The isolated and purified enzymes immobilized separately on a Ultrogel matrix and placed in an apparatus with UDP-gal, UDP-galNAc and lactose. This apparatus is operated at a temperature of 37° C., in the presence of manganese ions at a concentration of from 1–15 mmol/l for 35 h. The resulting product is isolated by ion-exchange chromatography.

EXAMPLE 5

Synthesis of a Ganglio-series Oligosaccharide

A β-1,4 N-acetylgalactosaminyltransferase is isolated from detergent-treated calf brain tissue, purified by DEAE chromatography and by affinity chromatography on immobilized lactose and UDP columns. A β-1,3 galactosyltransferase is isolated from embryonic chick brain. Purification is achieved by affinity columns of UDP and immobilized galNAc β-1,4 gal β-1,4 glc-1-R. The isolated and purified enzymes are immobilized separately on an Affigel matrix and placed in an apparatus with UDP-galNAc, UDP-gal and lactose. This apparatus is operated at a temperature of 37° C., in the presence of manganese ions at a concentration of from 1–15 mmol/l for 38 h. The resulting product is isolated by ion-exchange chromatography.

EXAMPLE 6

Synthesis of a Muco-series Oligosaccharide

A β-1,4 galactosyltransferase is isolated from hog gastric mucosa treated with 1% TRITON X-100, purified by DEAE chromatography and by affinity chromatography on immobilized lactose and UDP columns. A β-1,3 galactosyltransferase is isolated from hog gastric mucosa. Purification is achieved by affinity columns of UDP and immobilized gal β-1,4 gal β-1,4 glc-1-R. The isolated and purified enzymes are immobilized separately on a Ultrogel matrix and placed in an apparatus with UDP-gal and lactose. This apparatus is operated at a temperature of 37° C., in the presence of manganese ions at a concentration of from 1–15 mmol/l for 49 h. The resulting product is isolated by ion-exchange chromatography.

EXAMPLE 7

Synthesis of a Globoiso-series Oligosaccharide

A α-1,3 galactosyltransferase is isolated from detergent-treated rat intestine tissue, purified by DEAE chromatography and affinity chromatography on immobilized lactose and UDP columns. A β-1,3 N-acetylgalactosaminyltransferase is isolated from detergent-treated lymphosarcoma tissue. Purification is achieved by affinity columns of UDP and immobilized gal α-1,3 gal β-1,4 glc-1-R. The isolated and purified enzymes are immobilized separately on an Affigel matrix and placed in an apparatus with UDP-gal, UDP-galNAc and lactose. This apparatus is operated at a temperature of 37° C., in the presence of manganese ions at a concentration of from 1–15 mmol/l for 31 h. The resulting product is isolated by ion-exchange chromatography.

EXAMPLE 8

Synthesis of a Mucin-type Oligosaccharide

An α-1 N-acetylgalactosaminyltransferase is isolated from detergent-treated bovine intestine tissue, purified by DEAE and CM chromatography and affinity chromatography on a UDP column. A β-1,3 galactosyltransferase is isolated from detergent-treated submaxillary glands. Purification is achieved by affinity columns of UDP and immobilized galNAc β-1 threonine. The isolated and purified enzymes are immobilized separately on an Affigel matrix and placed in an apparatus with UDP-galNAc, UDP-gal and threonine. This apparatus is operated at a temperature of 37° C., in the presence of manganese ions at a concentration of from 1–15 mmol/l for 48 h. The resulting product is isolated by ion-exchange chromatography.

EXAMPLE 9

Synthesis of a Mucin lacNAc Series Oligosaccharide Intermediate

A β-1,6 N-acetylglucosaminyltransferase is isolated from pig gastric mucosa, purified by DEAE chromatography and by affinity chromatography on immobilized mucin-type gal galNAc and UDP columns. A β-1,4 galactosyltransferase is isolated from bovine milk. Purification is achieved by affinity columns of UDP and immobilized gal β-1,3 galNAc (glcNAc β-1,6)α-1-O-linked serine. The isolated and purified enzymes are immobilized separately on an Affigel matrix and placed in an apparatus with UDP-glcNAc, UDP-gal and mucin-type galNAc gal. This apparatus is operated at a temperature of 37° C., in the presence of manganese ions at a concentration of from 1–15 mmol/l for 35 h. The resulting product is isolated by ion-exchange chromatography.

EXAMPLE 10

Synthesis of Elongated Heparin

An α-1,4 N-acetylglucosaminyltransferase is isolated from detergent-treated mastocytomas tissue, purified by DEAE chromatography and affinity chromatography on immobilized heparin and UDP columns. A β-1,4 glucuronyltransferase is also isolated from mastocytomas tissue. Purification is achieved by affinity columns of UDP and immobilized glcNAc α-1,4 substituted heparin. The isolated and purified enzymes are immobilized separately on an Affigel matrix and placed in an apparatus with UDP-glcNAc, UDP-glucuronic acid and heparin. This apparatus is operated at a temperature of 37° C., in the presence of manganese ions at a concentration of from 1–15 mmol/l for 36 h. The resulting product is isolated by ion-exchange chromatography.

EXAMPLE 11

Synthesis of an Elongated Chondroitin Sulfate

A β-1,4 N-acetylgalactosaminyltransferase is isolated from detergent-treated cartilage tissue, purified by DEAE chromatography and affinity chromatography on immobilized chondroitin sulfate and UDP columns. A β-1,3 glucuronyltransferase is isolated from detergent-treated cartilage tissue. Purification is achieved by affinity columns of UDP and immobilized galNAc β-1,4 substituted chondroitin sulfate. The isolated and purified enzymes are immobilized separately on a Ultrogel matrix and placed in an apparatus with UDP-galNAc, UDP-glucuronic acid and chondroitin sulfate. This apparatus is operated at a temperature of 37° C., in the presence of manganese ions at a concentration of from 1–15 mmol/l for 27 h. The resulting product is isolated by ion-exchange chromatography.

EXAMPLE 12

Synthesis of Elongated Hyaluronic Acid

A β-1,4 N-acetylglucosaminyltransferase is isolated from detergent-treated connective tissue, purified by DEAE chromatography and by affinity chromatography on immobilized hyaluronic acid and UDP columns. A β-1,3 glucuronyltransferase is isolated from detergent-treated connective tissue. Purification is achieved by affinity columns of UDP and immobilized glcNAc β-1,4 substituted hyaluronic acid. The isolated and purified enzymes are immobilized separately on an Affigel matrix and placed in an apparatus with UDP-glcNAc, UDP-glucuronic acid and hyaluronic acid. This apparatus is operated at a temperature of 37° C., in the presence of manganese ions at a concentration of from 1–15 mmol/l for 33 h. The resulting product is isolated by ion-exchange chromatography.

EXAMPLE 13

Synthesis of Lewis$^y$

An α-1,2 fucosyltransferase, capable of transferring fuc to the terminal gal of lactose or Type II polylactosamine is isolated from COLO 201, a human tumor cell line, purified by DEAE chromatography and by affinity chromatography on immobilized polylactose and GDP columns. An α-1,3 fucosyltransferase capable of transferring fuc to the penultimate glcNAc of polylactosamine is isolated from COLO 205 a human colon tumor cell line. Purification is achieved by affinity columns of GDP and immobilized polylactose. The isolated and purified enzymes are immobilized separately on an Affigel matrix and placed in an apparatus with two or more equivalents of GDP-fuc and polylactose. This apparatus is operated at a temperature of 37° C., in the presence of manganese ions at a concentration of from 1–15 mmol/l for 33 h. The resulting product is isolated by ion-exchange chromatography.

EXAMPLE 14

Synthesis of Gal α Gal Epitope

A β-1,4 galactosyltransferase is isolated from bovine milk, purified by DEAE chromatography and by affinity chromatography on immobilized galNAc and UDP columns. An α-1,3 galactosyltransferase capable of transferring gal to gal β-1,4 galNAc or gal β-1,4 glcNAc is isolated from detergent-treated murine F9 cells. Purification is achieved by affinity columns of UDP and immobilized gal β-1,4 gal α-1,4 galNAc. The isolated and purified enzymes are immobilized separately on an Affigel matrix and placed in an apparatus with two or more equivalents of UDP-gal and gal β-1,4 galNAc. This apparatus is operated at a temperature of 37° C., in the presence of manganese ions at a concentration of from 1–15 mmol/l for 36 h. The resulting product is isolated by ion-exchange chromatography.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A method of adding monosaccharides to heparin, comprising:
   i) purifying an α-1,4 N-acetylglucosaminyltransferase by affinity chromatography on immobilized heparin and UDP columns;
   ii) purifying a β-1,4 glucuronyltransferase by affinity chromatography on UDP and immobilized glcNAc β-1,4 substituted heparin columns; and
   iii) reacting UDP-glcNAc, UDP-glucuronic acid and heparin in the presence of the purified α-1,4 N-acetylglucosaminyltransferase of step i) and the purified β-1,4 glucuronyltransferase of step ii).

2. A method of adding monosaccharides to heparin, comprising:
   i) purifying an α-1,4 N-acetylglucosaminyltransferase by DEAE chromatography and affinity chromatography on immobilized heparin and UDP columns;
   ii) purifying a β-1,4 glucuronyltransferase by affinity chromatography on UDP and immobilized glcNAc β-1,4 substituted heparin columns; and
   iii) reacting UDP-glcNAc, UDP-glucuronic acid and heparin in the presence of the purified α-1,4 N-acetylglucosaminyltransferase of step i) and the purified β-1,4 glucuronyltransferase of step ii).

3. The method of claim 1, further comprising isolating a heparin to which monosaccharides have been added.

* * * * *